(12) United States Patent
Hubers

(10) Patent No.: US 6,363,803 B1
(45) Date of Patent: Apr. 2, 2002

(54) VEHICLE MOUNTED SOIL SAMPLER

(76) Inventor: Elmer Hubers, 4786 NC 45 North, Pantego, NC (US) 27860

( * ) Notice: Subject to any disclaimer, the term of this patent is extended or adjusted under 35 U.S.C. 154(b) by 18 days.

(21) Appl. No.: 09/634,708

(22) Filed: Aug. 7, 2000

(51) Int. Cl.[7] .......................... G01N 1/04; G01F 15/04; E21B 7/24
(52) U.S. Cl. ..................... 73/864.43; 73/432.1; 175/19; 175/20
(58) Field of Search ........................... 73/864.43, 432.1; 175/19, 20

(56) References Cited

U.S. PATENT DOCUMENTS

| | | | |
|---|---|---|---|
| 3,344,875 A | | 10/1967 | Briner |
| 3,464,504 A | * | 9/1969 | Stange .......................... 173/28 |
| 3,593,809 A | | 7/1971 | Derry .......................... 175/113 |
| 4,333,541 A | * | 6/1982 | Doty .......................... 175/162 |
| 4,482,021 A | | 11/1984 | Repski ........................ 175/209 |
| 4,534,231 A | | 8/1985 | Jonsson et al. ........... 73/864.43 |
| 4,685,339 A | * | 8/1987 | Philipenko ............... 73/865.45 |
| 5,076,372 A | | 12/1991 | Hellbusch ..................... 175/20 |
| 5,394,949 A | | 3/1995 | Wright et al. .................. 175/20 |
| 5,435,399 A | | 7/1995 | Peterson et al. ............... 175/20 |
| 5,931,236 A | | 8/1999 | Mahlum et al. ............... 175/20 |
| 5,950,741 A | | 9/1999 | Wright et al. .................. 175/20 |

* cited by examiner

Primary Examiner—Hezron Williams
Assistant Examiner—Katina Wilson
(74) Attorney, Agent, or Firm—Tom Hamill, Jr.

(57) ABSTRACT

A vehicle mounted soil sampler is provided. The soil sampler is designed to be mounted inside the vehicle proximal the operator. A mounting plate secures the soil sampler to the interior of the vehicle. A opening is provided in the floorboard underneath the soil sampler to permit the soil sampler to leave the vehicle, take a sample, and return to the vehicle with the sample. The soil sampler includes a first hydraulic motor and a second hydraulic motor. The first hydraulic motor is operates a chain drive which moves a guide member in an upward or downward fashion. The guide member is affixed to the auger assembly. The auger assembly includes an auger, a second hydraulic motor which rotates the auger as well as a sample chamber. The operator will drive the vehicle to a location where a soil sample is desired to be taken. The first hydraulic motor is actuated, lowering the auger assembly through the floor of the vehicle to the soil surface. The second hydraulic motor rotates the auger, while the action of the first hydraulic motor drives the auger assembly downward, and the auger bites into the soil, taking the sample. The first hydraulic motor is then reversed, bringing the auger back into the sample chamber and then the auger assembly back into the vehicle. The soil sample is retained in the sample chamber. The sample is then removed and categorized. The operator would then drive the vehicle to a second sample point and repeat the process. The vehicle may include GPS or other precision locating equipment to permit samples to be taken at precise locations. The soil sample will be analyzed in a laboratory.

10 Claims, 5 Drawing Sheets

VEHICLE MOUNTED SOIL SAMPLER

BACKGROUND OF THE INVENTION

1. Field of the Invention

The present invention relates generally to soil sampling devices, and more particularly, to a soil sampling device that is mounted inside of a vehicle especially adapted to effect the taking of soil samples at multiple locations.

2. Description of the Prior Art

In the farming industry it is well known to supplement the arable land with fertilizer and other chemical compositions to ensure crop efficacy, disease free crops and pest free crops. The cost of such fertilizers and the like is great due to the large amount of arable land requiring treatment. Due to the cost of such chemicals, it is desirable to determine the amount of fertilizer or other chemical components located in the soil of arable land prior to further treatment. In this way, areas which require greater amounts of fertilizer will become known to the farmer and sufficient quantities may be applied. Likewise, areas which still have sufficient amounts of fertilizer need not be treated. Accurately determining the soil chemistry at specific locations on the farm is a desirable piece of knowledge for the farmer to have.

In the past, fields have been fertilized equally according to standard methodologies such as those put forth by the United States Department of Agriculture. Now, the soil may be sampled according to a specific grid and greater or lesser amounts of fertilizer may be applied where it specifically warranted.

SUMMARY OF THE INVENTION

To achieve the foregoing and other advantages, the present invention, briefly described, provides a vehicle mounted soil sampler. The soil sampler is designed to be mounted inside the vehicle proximal the operator. A mounting plate secures the soil sampler to the interior of the vehicle. A opening is provided in the floorboard underneath the soil sampler to permit the soil sampler to leave the vehicle, take a sample, and return to the vehicle with the sample. The soil sampler includes a first hydraulic motor and a second hydraulic motor. The first hydraulic motor is operates a chain drive which moves a guide member in an upward or downward fashion. The guide member is affixed to the auger assembly. The auger assembly includes an auger, a second hydraulic motor which rotates the auger, and a sample chamber. The operator will drive the vehicle to a location where a soil sample is desired to be taken. The first hydraulic motor is actuated, lowering the auger assembly through the floor of the vehicle to the soil surface. The second hydraulic motor rotates the auger, while the action of the first hydraulic motor drives the auger assembly downward, and the auger bites into the soil, taking the sample. The first hydraulic motor is then reversed, bringing the auger back into the sample chamber and then the auger assembly back into the vehicle. The soil sample is retained in the sample chamber. The sample is removed and categorized. The operator would then drive the vehicle to a second sample point and repeat the process. The vehicle may include GPS or other precision locating equipment to permit samples to be taken at precise locations.

The soil sampler is constructed as followed. A mounting plate is secured inside the vehicle. The mounting plate is secured to a generally rectangular elongated hollow element or tube. The tube has a bottom portion and a top portion. The bottom portion is connected to the mounting plate. The top portion includes mounting plenum for mounting a first hydraulic motor. The first hydraulic motor is connected to a top sprocket which resides in a top sprocket housing. A bottom sprocket is located in a bottom sprocket housing located proximal the tube bottom portion. The top sprocket and the bottom sprocket are connected by a travel chain. One portion of the chain resides within the hollow tube and the other portion resides outside the hollow tube. When the first hydraulic motor is actuated, the chain will travel in a first direction.

A traveling rectangular hollow element fits coaxially atop the hollow tube and is secured to the chain by a mounting plate. The mounting plate is further secured to the auger assembly. As the chain moves so does the auger assembly. The traveling element slides atop the hollow tube which acts as a guide member.

The auger assembly includes a second hydraulic motor mounted on a motor mounting plate. The second hydraulic motor is operatively connected to the auger and when actuated causes the auger to rotate. The motor mounting plate is a L-shaped member and is connected to a U-shaped element which is connected to the chain and the traveling member. Both the L-shaped member and the U-shaped member include an aperture to permit the motor shaft and auger to pass through respectively.

A first, second and third guide rod are provided, each with a top element, an intermediate element and a lower element. The upper element of the first, second and third guide rods are slidably disposed in the generally U-shaped element. The first, second and third guide rods are located equidistant from the centrally located auger. The lower elements of the first, second and third guide rods are connected through apertures located on the top portion of the sample basket. The intermediate element of the first, second and third guide rods include shaft collars or stop members located thereon.

The sample basket may be cylindrical or rectangular and has a top portion, a sidewall and a bottom portion. The top portion includes a central aperture to permit the auger to pass there through. The top portion's diameter is greater than the diameter of the sample basket and has three apertures located on. These apertures are designed to receive the first, second and third guide rods in a secured fashion thereon. The bottom portion includes a central aperture to permit the auger to pass there through. The bottom portion further includes a right side and a left side. The right side is hinged permitting the bottom portion to open in a pivotal fashion about the right side. The left side includes means to secure the bottom portion to the sidewall.

The drive chain is actuated by the first hydraulic motor causing the traveling element to move the auger assembly to the ground sample point. At this point, the second hydraulic motor engages, causing the auger to rotate. The first hydraulic motor drives the auger assembly downward and the auger bites into the earth. This continues as the traveling element is lowered by the first hydraulic motor. Concurrently, the guide rods begin to slide upwardly through the three apertures located on the generally U-shaped element. When the guide rods reach a certain distance, the stop members located on each of the guide rods will coact with the bottom portion of the generally U-shaped element This stops the downward motion of the auger assembly. At this point the first hydraulic motor is reversed, causing the auger to return to inside the sample basket bringing with it the soil sample taken at that location. The second hydraulic motor is disengaged, stopping the rotation of the auger. The first hydraulic motor continues, bringing the auger assembly and sample chamber back into the vehicle. At this point the bottom portion of the sample chamber is opened and the soil sample is removed and cataloged with respect to location, date, current weather conditions etc. The vehicle would then move to a second location and another sample would be taken. The vehicle may be equipped with GPS or other expert systems which would give exact sampling location coordinates.

The samples would then be taken to a laboratory for nutrient analysis and soil pH. The laboratory would recommend which nutrient or combination thereof would be added to the soil at that location. Some of the compositions which may be considered to be added include, but are not limited to, nitrogen, phosphorous, potash, copper, zinc, manganese, and sulfur.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will form the subject matter of the claims appended hereto.

In this respect, before explaining the invention in detail, it is to be understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which this disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a portable soil sampler which may be mounted in place of a passenger seat in the interior of a vehicle.

It is an object of the present invention to provide a portable soil sampler which may be mounted on the exterior of a vehicle.

It is an object of the present invention to provide a portable soil sampler with two hydraulic motors, one to raise and lower the auger assembly through the floor of the vehicle to the sample point and one to actuate the rotation of the auger to take the soil sample.

It is an object of the present invention to provide a portable soil sampler with a traveling member affixed intermediate the chain and the auger assembly, the chain moving about an upper and lower sprocket due to the action of one of the hydraulic motors, the motor being reversible, causing the chain and hence the auger assembly to move in an upward and downward direction.

It is an object of the present invention to provide a portable soil sampler which may quickly and efficiently take multiple soil samples at a plurality of locations without the operator leaving the vehicle.

It is an object of the present invention to provide a soil sampler which includes GPS or other precision position acquisition means, to permit the location of the soil sample to be accurately determined.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawings wherein.

DESCRIPTION OF THE PREFERRED EMBODIMENT

With reference now to the drawings, a portable soil sampler embodying the principles and concepts of the present invention will be described.

Figure 1:
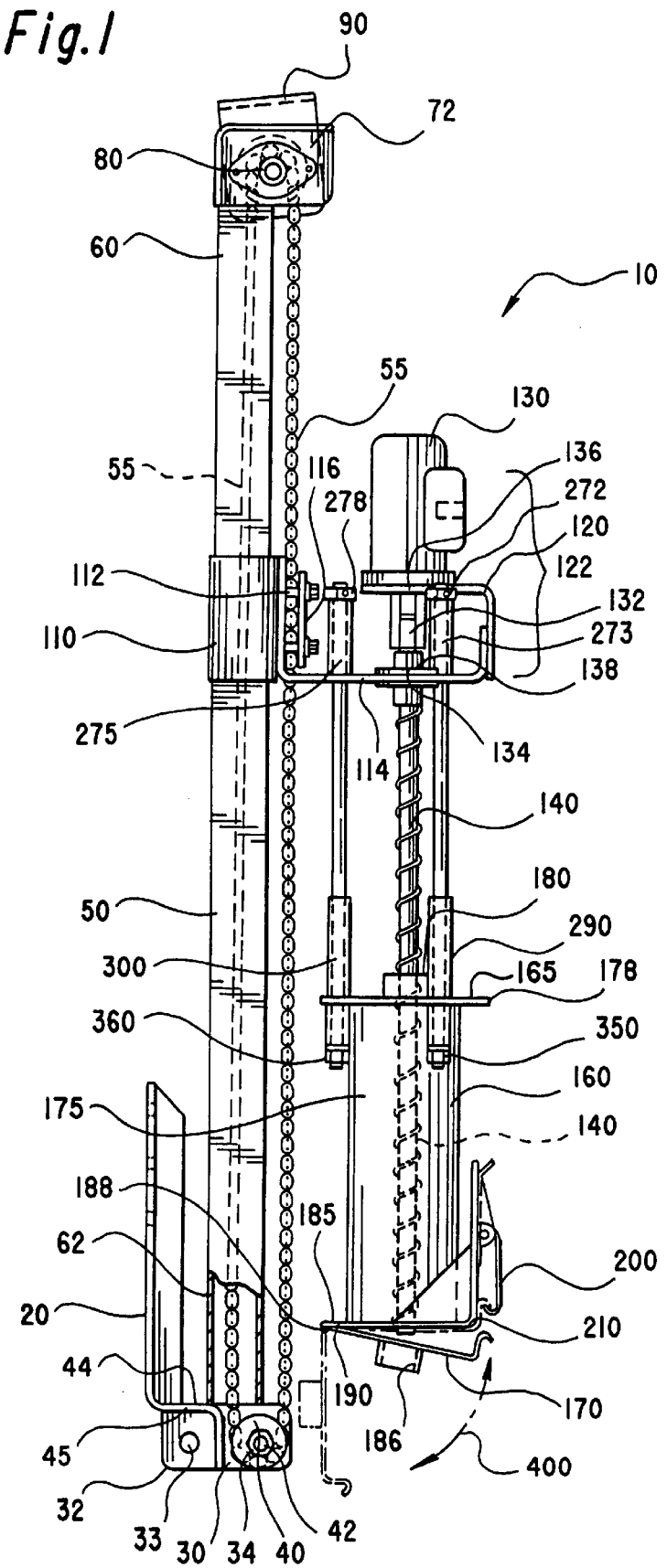
FIG. 1 is a side view showing the portable soil sampler of the invention.
Figure 2:
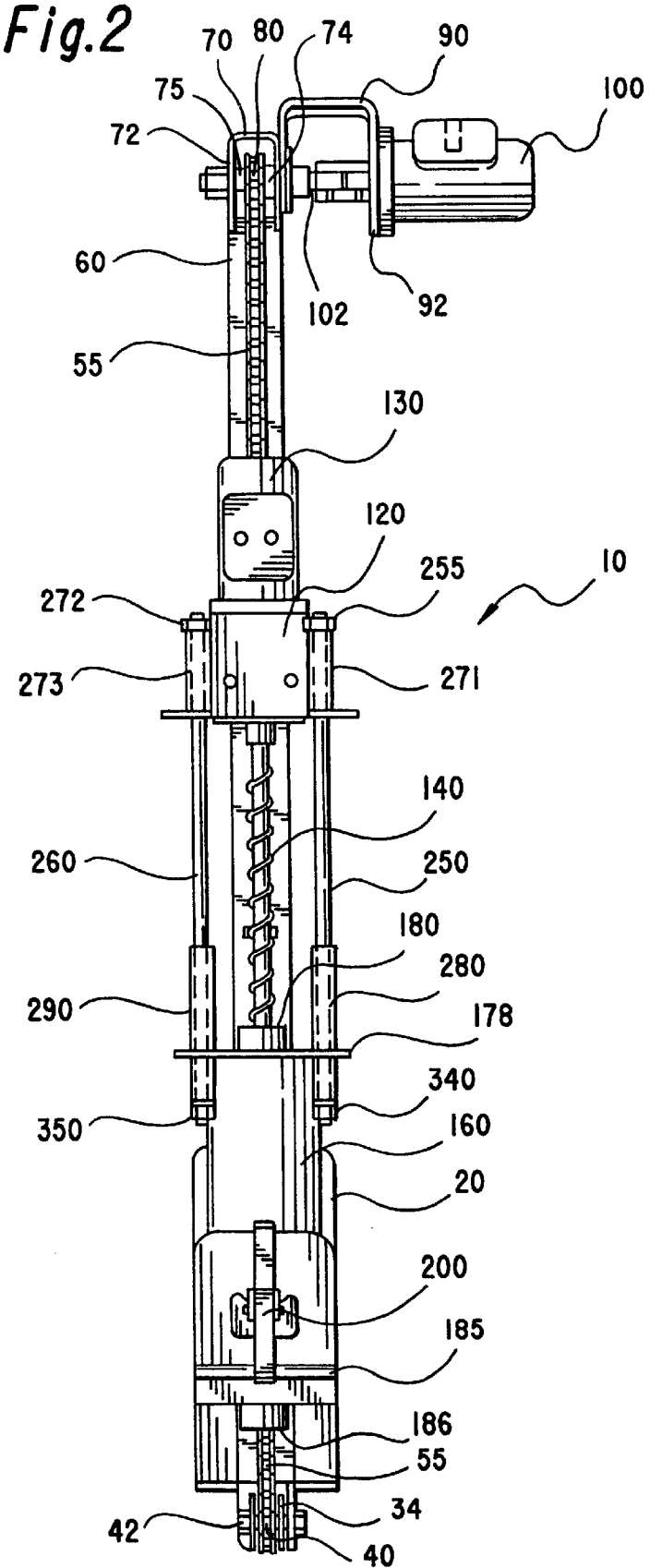
FIG. 2 is a front view showing the portable soil sampler of the invention.
Figure 3:
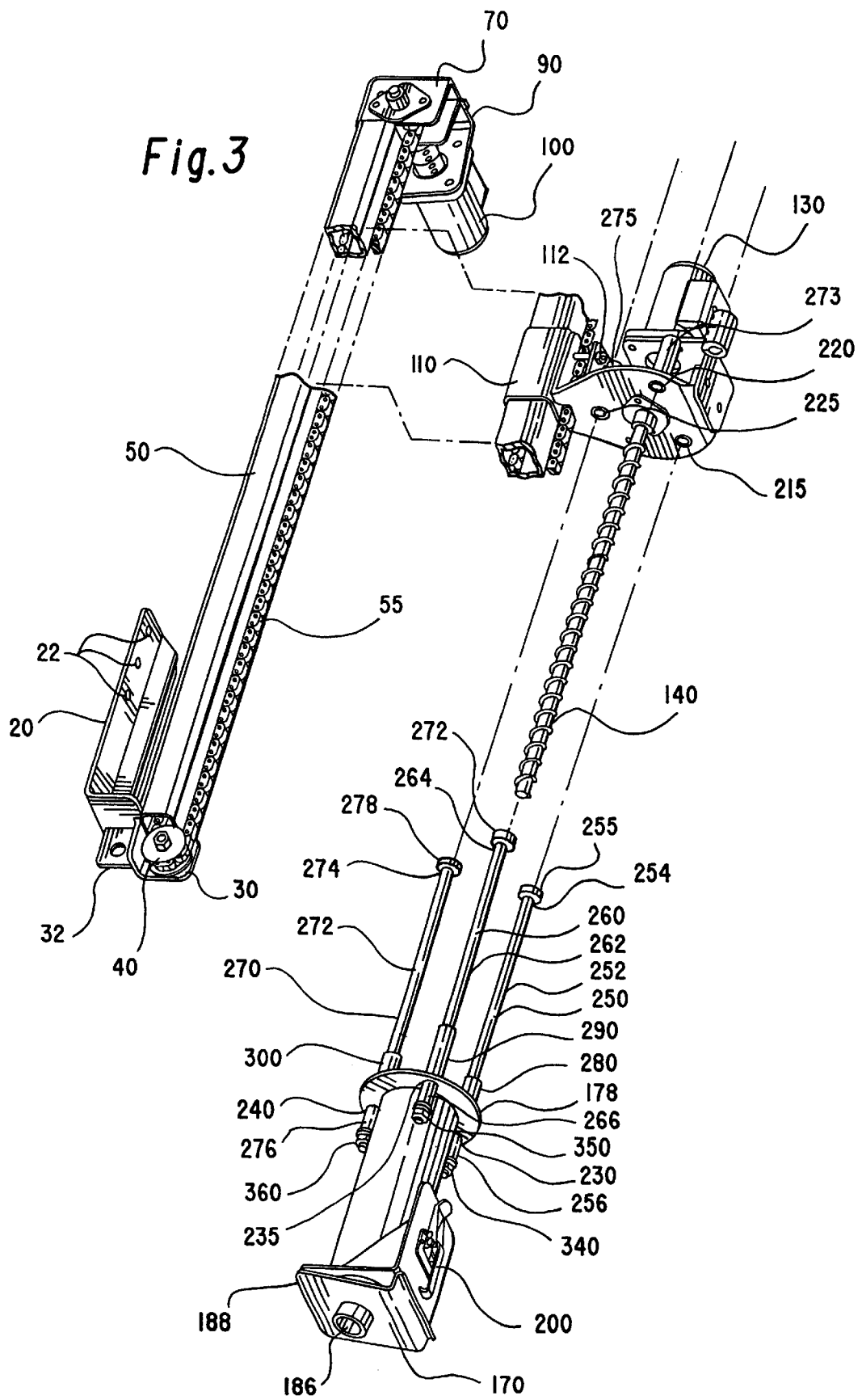
FIG. 3 is an exploded view showing the components of the portable soil sampler of the invention.

Turning initially to FIGS. 1–3, there is shown the portable soil sampler of the invention generally designated by reference numeral 10. In its preferred form, the portable soil sampler 10 includes an L-shaped mounting plate 20 for mounting to the vehicle interior along the chassis or other hard point. The mounting plate 20 may be secured by a plurality of mechanical fasteners 24 passing through a plurality of first apertures 22 located on the L-shaped mounting plate 20.

It is to be understood that the portable soil sampler 10 may be also mounted outside a vehicle, by attaching L-shaped mounting plate 20 to the exterior of a vehicle at an appropriate location for support.

The L-shaped mounting plate 20 has a bottom portion which includes a a support element 32 and a sprocket mounting plate 30 mounted thereon. The sprocket mounting plate 30 includes a rotatable bearing 34, the rotatable bearing 34 having a rod element 42 supported thereon, the rod element 42 having a lower sprocket 40 mounted thereon. The support element 32 includes a support shaft 37 which connects to the chassis at connector 38. The support shaft 37 gives the portable soil sampler 10 stability and structural support when the vehicle is in use and when the portable soil sampler 10 is in use.

The L-shaped mounting plate 20 includes a foot 45. The top surface 44 of the foot 45 of the L-shaped mounting plate 20 includes an elongated hollow element 50 permanently disposed thereon. The elongated hollow element 50 has a generally square cross section and receives the traveling chain 55 therein. The central hollow portion is disposed above the lower sprocket 40, permitting the chain 55 to move freely without coacting with the interior sidewalls of the elongated hollow element 50.

The elongated hollow element 50 has an upper region 60 and a lower region 62. The upper region 60 is secured to a first C-shaped element 70 which includes a pair of rotatable bearing elements 72 & 74 disposed on opposite sides which have a rod member 75 passing there through. The rod member 75 has an upper sprocket 80 mounted centrally thereon. The upper sprocket 80 is disposed above the elongated hollow element 50, in such a fashion to permit the chain 55 to move freely without coacting with the interior sidewalls of the elongated hollow element 50.

A second C-shaped element 90 is connected to the first C-shaped element 70. A first motor 100 is mounted to the distal portion 92 of the second C-shaped element 90. The first motor 100 has a rotatable shaft 102 which is operatively connected to the rod member 75. When the first motor 100 is actuated, the upper sprocket 80 rotates, causing the chain 55 to move about the upper sprocket 80 and the bottom sprocket 40. The first motor 100 can rotate the upper sprocket 80 in both directions, which means that the chain 55 can travel in both an upward and a downward fashion.

A traveling member 110 is provided on the outside of the elongated hollow element 50. The traveling member 110 is dimensioned such that it can freely move up and down on the elongated hollow element 50 from the lower portion 62 to the upper portion 60. The traveling member 110 is connected to a U-shaped element 114. A plate 116 secures the chain 55 to the traveling member 110 through the U-shaped element 114 by fasteners 112. This assembly basically places the first motor in a first mechanical communication with the auger assembly 122. Other means to convert the bidirectional rotation of the first hydraulic motor to raise and lower the auger assembly may be provided.

The U-shaped element 114 is the foundation for the auger assembly or platform 122. The U-shaped element 114 is connected to a L-shaped element 120. The L-shaped element 120 has a second motor 130 mounted thereon and includes a second aperture 136 through which the second motor 130 shaft 132 passes. An auger 140 is attached to the second motor shaft 132. A third aperture 138 with a rotatable bearing 134 is provided through the U-shaped element 114 which the upper portion of the auger or other boring device 140 passes.

The U-shaped element 114 resides above a soil sample canister 160. The soil sample canister 160 is generally cylindrical, has a top element 165, a bottom element 170 and a sidewall 175. The top element 165 includes a top flange 178 which extends beyond the sidewall 175. The top element 165 has a fourth aperture 180 disposed centrally thereon which permits the auger 140 to pass there through. The bottom element 170 includes a bottom flange 185 which extends beyond the sidewall 175. The bottom element 170 has a fifth aperture 186 disposed centrally thereon which permits the auger 140 to pass there through. The bottom element 170 is attached to the sidewall 175 by a hinge 188 on a first side 190 and by a mechanical locking means 200 on a second side 210. The bottom element 170 may rotate 400 to an open and closed position. When the bottom element 170 is closed, the soil is retained in the soil sample canister 160. When the bottom element 170 is opened, the soil which has been collected in the soil sample canister 160 may be removed, catalogued, stored, and tested.

The U-shaped element 114 includes a sixth aperture 215, a seventh aperture 220 and an eighth aperture 225 located one hundred and twenty (120) degrees apart.

The top flange includes a ninth aperture 230, a tenth aperture 235 and an eleventh aperture 240 spaced one hundred and twenty (120) degrees apart.

The sixth aperture 215 is located directly above the ninth aperture 230. The seventh aperture 220 is located directly above the tenth aperture 235. The eighth aperture 225 is located directly above the eleventh aperture 240.

A first rod 250 has a top portion 254, an intermediate portion 252, and a bottom portion 256. A second rod 260 has a top portion 264, an intermediate portion 262 and a bottom portion 266. A third rod 270 has a top portion 274, an intermediate portion 272 and a bottom portion 276.

The first rod top portion 254 includes a first rod top sleeve 271. The first rod top sleeve 271 is secured atop the U-shaped element 114. The first rod top stop means 255 prevents the first rod 250 from sliding through the first rod top sleeve 271 in a downward fashion, and the first rod top sleeve 271 spaces the first rod 250 by a first vertical distance. The first rod top sleeve 271 is identical to the second rod top sleeve 270 and the third rod top sleeve 275.

The second rod top portion 264 includes a second rod top sleeve 273. The second rod top sleeve 273 is secured atop the U-shaped element 114. The second rod top stop means 272 prevents the second rod 260 from sliding through the second rod top sleeve 273 in a downward fashion, and the second rod top sleeve 273 spaces the second rod 260 for a second vertical distance.

The third rod top portion 274 includes a third rod top sleeve 275. The third rod top sleeve 275 is secured atop the U-shaped element 114. The third rod top stop means 278 prevents the third rod 270 from sliding through the third rod top sleeve 275 in a downward fashion, and the third rod top sleeve 275 spaces the third rod 270 by a third vertical distance. The first vertical distance, second vertical distance and third vertical distance are identical.

The first rod 250 is slidably disposed through the U-shaped element 114 at the sixth aperture 215. The second rod 260 is slidably disposed through the U-shaped element 114 at the seventh aperture 220. The third rod 270 is slidably disposed through the U-shaped element 114 at a eighth aperture 225.

The first rod bottom portion 256 includes a first bottom portion 280 which is slidingly received over the first rod 250. The second rod bottom portion 266 includes a second bottom portion sleeve 290 which is slidingly received over the second rod 260. The third rod bottom portion 276 includes a third bottom-portion sleeve 300 which is slidingly received over the third rod 270. The first sleeve 280, second sleeve 290 and third sleeve 300 are chosen to be of identical lengths, and can be chosen to be longer or shorter.

The first rod bottom member 256 includes a first end element 340 secured thereto. The second rod bottom member 266 includes a second end element 350 secured thereto. The third rod bottom member 276 includes a third end element 360 secured thereto.

When the first motor 100 is engaged, the traveling member 110 goes downward, lowering the auger assembly 122. When the soil sample canister 160 bottom element 170 coacts with the ground, the second motor 130 is actuates which causes the auger 140 to rotate. The first motor 100 continues to bring the auger assembly 122 downward, and the first rod 250, the second rod 260 and the third rod 270, slidingly pass through the sixth aperture 215, seventh aperture 220 and eighth aperture 225 respectively. At this point, the auger 140 bites into the soil. When the first sleeve 280, second sleeve 290, and third sleeve 300 come into contact with the bottom of the U-shaped element 114, the auger 140 has drilled to its maximum depth into the soil. At this point the first motor 100 is reversed, raising the auger assembly 122. This has the effect of retracting the auger 140 proper back inside the soil sample canister 160 and bringing the soil sample canister 160 back into the vehicle.

When the auger 140 returns to the soil sample canister 160, the sampled soil falls from the auger 140 and is retained in the soil sample canister 160. The vehicle operator 420 will take the soil sample and place it in a container along with information as to where the sample was taken, time of day, weather conditions, etc. The vehicle operator 420 then moves the vehicle 410 to the next desired sample location and begins the sampling process again. Several samples may be added together to form an average.

The operation of the portable soil sampler 10 is controlled by the vehicle operator 420. Ancillary devices such as a GPS 500 may be employed to accurately determine the location that the soil sample is being taken at. A soil sampler controller, which controls the raising and lowering of the auger assembly (the first motor), and the rotation of the auger (the second motor) is selectively engaged to employ the soil sampler by the vehicle operator. The soil sampler controller of the instant invention may, in certain conditions, be automatically controlled by a computer employing appropriate sample taking programming.

The first motor 100 and the second motor 130 are chosen to be reversible hydraulic motors. They could be other types of motors, including, but not limited to, electric motors, pneumatic motors, and stepper motors.

Figure 4:
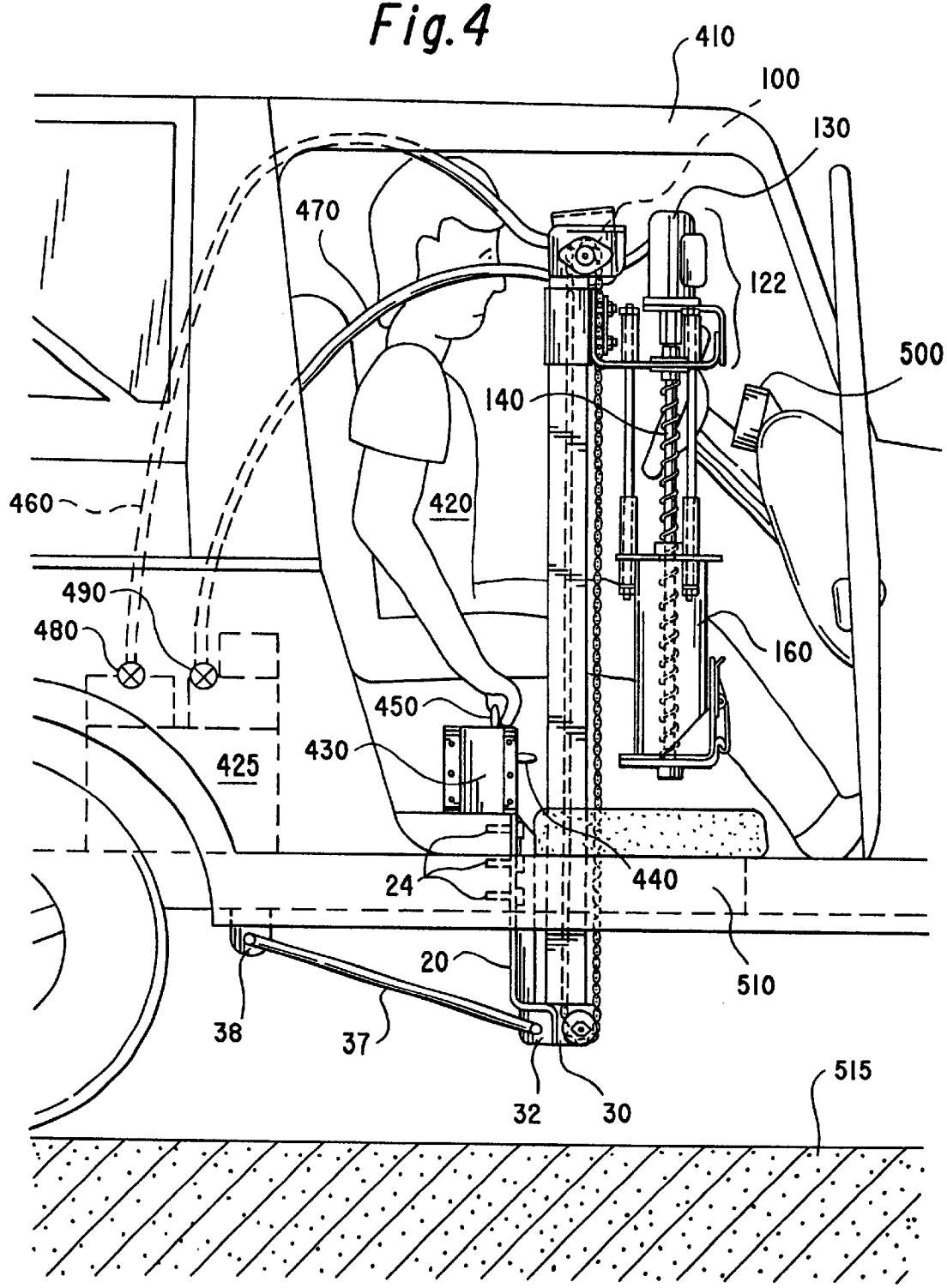
FIG. 4 is a view of the portable soil sampler being utilized with a vehicle, the portable soil sampler being in its neutral position.
Figure 5:
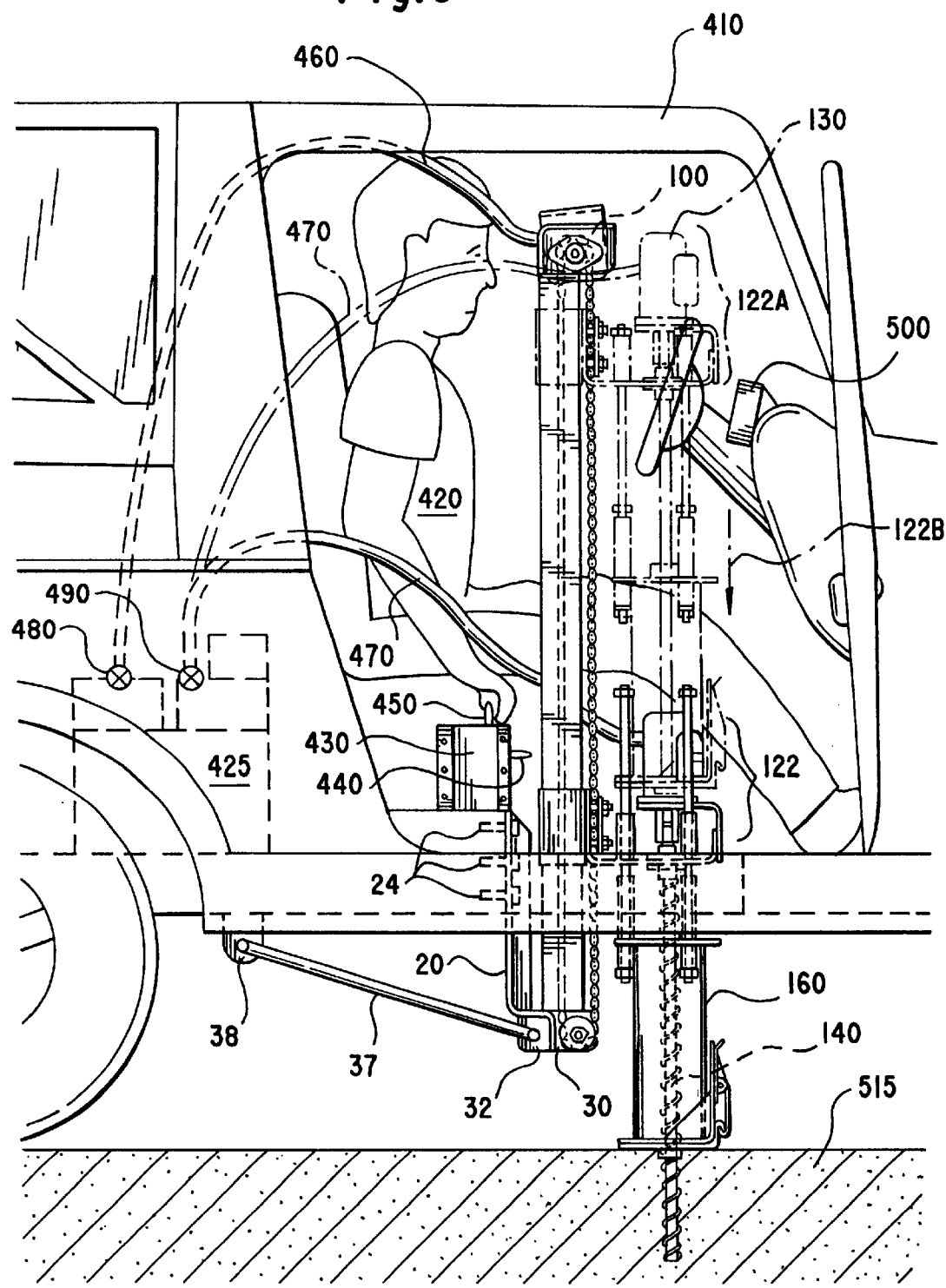
FIG. 5 is a view of the portable soil sampler being utilized with a vehicle, the portable soil sampler being in its sampling position.

Referring now specifically to FIGS. 4 and 5, the portable soil sampler 10 is shown mounted in the vehicle 410 with the operator 420. A power unit 425 for the hydraulic system is provided. The power unit includes a 2-way hydroelectric valve for splitting the hydraulic fluid into a first hydraulic stream 460 to the first hydraulic motor 100 and a second hydraulic stream 470 to the second hydraulic motor 130. Each stream has a flow control valve, the first hydraulic control valve 480 to control the speed of the up and down motion of the auger assembly 122, and the second hydraulic control valve 490 to control the speed and direction of rotation of the auger 140 itself. A 12 volt hydraulic motor is provided which runs off the vehicle battery. The hydraulic motor in turn runs a hydraulic pump which is connected to the above mentioned 2 way hydroelectric valve.

The operator 420 employs several control switches on a control box 430 to operate the portable soil sampler 10. An on-off switch 440 is provided on the control box 430 for providing power to the power unit. A 2 way toggle switch 450 is provided on the control box 430 as well. It has a forward, neutral and rear position. The 2 way toggle switch 450 when pushed forward causes the chain 55 to move the auger assembly 122 downward and when pushed rearwardly causes the chain 55 to move the auger assembly 122 upward. A microswitch is also provided which prevents the pump motor from turning off when the auger assembly is in the lowered position.

FIG. 4 shows the portable soil sampler 10 in the vehicle. In this position, the vehicle 410 may travel over roads or off road. The vehicle 410 stops above a preferred location for a soil sample. The operator 420 may select the position of the sample by use of the GPS 500. The auger assembly 122 is in its first position inside the vehicle 410. The auger assembly 122 and soil sample canister 160 reside above an opening 510 in the floorboard of the vehicle 410. When the vehicle 410 is in motion, a covering may be placed in the opening 510 to prevent debris, water or other material from entering the vehicle 410.

FIG. 5 shows the portable soil sampler 10 taking a soil sample. The auger assembly 122 is shown residing proximal the opening 510 in the floorboard. The original location of the auger assembly 122A is shown in phantom, and it travels in the direction indicated by 122B. The auger 140 is shown disposed in the soil 515. When the auger assembly 122 is withdrawn from the soil 515, the auger 140 withdraws back into the soil sample canister 160, depositing the soil sample there within.

Again, it is to be understood that the instant invention may be mounted on the exterior of a vehicle as well. Additionally, it has been considered that the instant invention may be mounted on a robotic platform, and its sampling may be performed remotely by a wireless communication system. This would be advantageous for sampling in a dangerous environment, an environment where a conventional vehicle cannot physically traverse, or other applications.

Additionally, the first and second hydraulic motors may be replaced by electric motors. In this embodiment, the hydraulic fluid assembly required to power the hydraulic motors would be replaced by an analogous electrical assembly.

It is apparent from the above that the present invention accomplishes all of the objectives set forth by providing a portable soil sampler with a traveling member affixed intermediate the chain and the auger assembly, the chain moving about an upper and lower sprocket due to the action of one of the hydraulic motors, the motor being reversible, causing the chain and hence the auger assembly to move in an upward and downward direction.

With respect to the above description, it should be realized that the optimum dimensional relationships for the parts of the invention, to include variations in size, materials, shape, form, function and manner of operation, assembly and use, are deemed readily apparent and obvious to those skilled in the art, and therefore, all relationships equivalent to those illustrated in the drawings and described in the specification are intended to be encompassed only by the scope of appended claims.

While the present invention has been shown in the drawings and fully described above with particularity and detail in connection with what is presently deemed to be the most practical and preferred embodiment of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed as being new and desired to be protected by Letters Patent of the United States is as follows:

1. A vehicle mounted soil sampler comprising:
   a first motor,
   said first motor connected to a first sprocket,
   a second sprocket,
   a chain, said chain disposed about said first sprocket and said second sprocket,
   a traveling member and a guide rod, said traveling member connected to said chain, said traveling member further slidably disposed on said guide rod, a second motor, said second motor disposed upon a platform, said second motor operatively connected to an auger, said platform connected to said traveling member, a canister, said canister residing below said second motor, said auger passing through said canister, said canister connected to said platform by a plurality of rods, whereby when said first motor is actuated, said first motor causes said first sprocket to rotate, causing said chain to move, said chain causing said traveling member to move in a downward manner, causing said platform to lower, and when said second motor is actuated, said second motor causes said auger to rotate, when said platform is lowered sufficiently, said canister abuts the soil and said auger passes through said canister and penetrates the soil, while said plurality of rods slidably move upwardly through said platform, when said auger is at a desired depth, said first motor is reversed, causing said first sprocket to rotate in the opposite direction, causing said chain to move in the opposite direction, said chain causing said traveling member to move in an upward manner, causing said platform to rise, causing said plurality of rods to slidably move downwardly through said platform, returning said auger to said canister, where said first and said second motor are disengaged, leaving a soil sample in said canister.

2. A soil sampler adapted to be mounted on a vehicle comprising, a first motor, said first motor in a first mechanical communication with a sample assembly, said first mechanical communication means includes a chain mounted between a first sprocket and a second sprocket, said chain is further connected to a traveling member, said traveling member nested atop a hollow element, said hollow element located intermediate said first sprocket and said second sprocket, a second motor, said second motor in a second mechanical communication with a boring device, said second motor located on said sample assembly, said first motor adapted to cause said sample assembly to be lowered and raised, said second motor adapted to cause rotation of said boring device, whereby said first motor lowers said sample assembly to the soil, said boring device bores into the soil, said first motor raises said sample assembly, retaining a soil sample in said sample assembly.

3. A soil sampler as claimed in claim 2 wherein said sample assembly includes a sample retaining canister, said boring device reciprocating between inside said sample retaining canister and the soil, whereby when said sample assembly is lowered, and said boring device exits said sample retaining canister and bores into the soil, and when said sample assembly is raised, said boring device returns to said soil retaining canister, depositing a soil sample therein.

4. A soil sampler as claimed in claim 2 wherein said first sprocket and said second sprocket are positioned so that a first portion of said chain is located centrally in said hollow element and a second portion of said chain is located outside said hollow element.

5. A soil sampler as claimed in claim 4 wherein said traveling member is moved downwardly about said hollow element when said first motor is actuated, and said traveling member is moved upwardly when said first motor is reversed.

6. A soil sampler as claimed in claim 5 wherein said hollow element is mounted perpendicularly to the soil by a mounting plate.

7. A soil sampler as claimed in claim 6 wherein said first motor is connected to said first sprocket.

8. A soil sampler as claimed in claim 7 wherein said second mechanical communication means includes a sleeve which connects the second motor to said boring device, permitting said second motor to rotate said boring device.

9. A soil sampler as claimed in claim 8 wherein said sample retaining canister includes a bottom side, said bottom side being selectively pivotably attached to said sample retaining canister, wherein said bottom side may be opened to remove the soil retained in said sample retaining canister for testing.

10. A soil sampler as claimed in claim 9 wherein said sample assembly includes means to adjust the depth of penetration into the soil of said boring device.

\* \* \* \* \*